(12) United States Patent  
Völker

(10) Patent No.: US 7,741,859 B2
(45) Date of Patent: Jun. 22, 2010

(54) DETECTION OF SEALING BY MEANS OF NOISE ANALYSIS

(75) Inventor: Moritz Völker, München (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 101 days.

(21) Appl. No.: 11/411,092

(22) Filed: Apr. 26, 2006

(65) Prior Publication Data

US 2006/0237331 A1     Oct. 26, 2006

(30) Foreign Application Priority Data

Apr. 26, 2005   (DE) ....................... 10 2005 019 191

(51) Int. Cl.
    *G01R 27/08*     (2006.01)
    *G01N 27/26*     (2006.01)
(52) U.S. Cl. .................... 324/713; 324/700; 205/775
(58) Field of Classification Search ........... 324/713, 324/691, 649, 600, 71.2, 700, 216, 237, 238, 324/240, 635, 644, 662, 671, 699, 716, 718; 205/775, 775.5, 776.5
    See application file for complete search history.

(56) References Cited

U.S. PATENT DOCUMENTS

| | | | | |
|---|---|---|---|---|
| 4,806,849 A * | 2/1989 | Kihira et al. | ................. | 324/700 |
| 5,187,096 A | 2/1993 | Giaever et al. | | |
| 5,221,893 A * | 6/1993 | Kondou et al. | ............. | 324/71.2 |
| 5,888,374 A * | 3/1999 | Pope et al. | ............... | 205/775.5 |
| 6,134,971 A * | 10/2000 | Misra et al. | .................... | 73/777 |
| 6,328,878 B1 * | 12/2001 | Davis et al. | ............. | 205/776.5 |
| 6,411,110 B1 * | 6/2002 | Gilton | ........................ | 324/718 |
| 6,611,151 B1 | 8/2003 | Ruedisueli et al. | | |

| | | | | |
|---|---|---|---|---|
| 2003/0113833 A1 | 6/2003 | Oka et al. | | |
| 2005/0247573 A1 * | 11/2005 | Nakamura et al. | ....... | 205/777.5 |

OTHER PUBLICATIONS http://en.wikipedia.org/wiki/Electrical_noise.*
Yang, M. et al., "Influence of geometry and environmental parameters on the quality of signature patterns for single neuron chemical sensors," Sensors and Actuators B, Jan. 3, 2005, vol. 104 No. 1, pp. 163-171.
Giaever, I. et al., "A morphological biosensor for mammalian cells," Nature, Dec. 9, 1993, vol. 366 No. 9, pp. 591-592.
Wenger, J. et al., "Barrier function of porcine choroids plexus epithelial cells is modulated by camp-dependent pathways in vitro," Brain Research, 2000, vol. 853, pp. 115-124.
Buitenweg, J.R. et al., "Measurement of sealing resistance of cell-electrode interfaces in neuronal cultures using impedance spectroscopy," Medical and Biological Engineering and Computing, Sep. 1, 1998, vol. 36 No. 5, pp. 630-637.
John H. T. Luong "An Emerging Impedance Sensor Based on Cell-Protein Interactions: Applications in Cell Biology and Analytical Biochemistry"; Analytical Letters, vol. 36, Issue 15 2003, pp. 3147-3164 (abstract only available).
Jean Paul Thiery "Cell adhesion in cancer"; Comptes Rendus Physique, 2003, pp. 289-304 (abstract only available).
R. Ehret et al. "On-line control of cellular adhesion with Impedance measurements using interdigitated electrode structures"; Cellular Engineering, 1998, pp. 365-370.
R. Lind at al. "Single cell mobility and adhesion monitoring using extracellular electrodes", BIosensors & Bioelectronics. 1991, pp. 359-367.
Applied Bio Physics 2004 - Brochure "Ecis - an automated method to monitor cell behavior".
Citation list from Retro Search of Jun. 2004.

* cited by examiner

*Primary Examiner*—Hoai-An D Nguyen
(74) *Attorney, Agent, or Firm*—Millen, White, Zelano & Branigan, P.C.

(57) ABSTRACT

The invention relates to a method for determining the sealing of a substance on a support by determining the electrical noise.

38 Claims, 6 Drawing Sheets

DETECTION OF SEALING BY MEANS OF NOISE ANALYSIS

Figure 1:
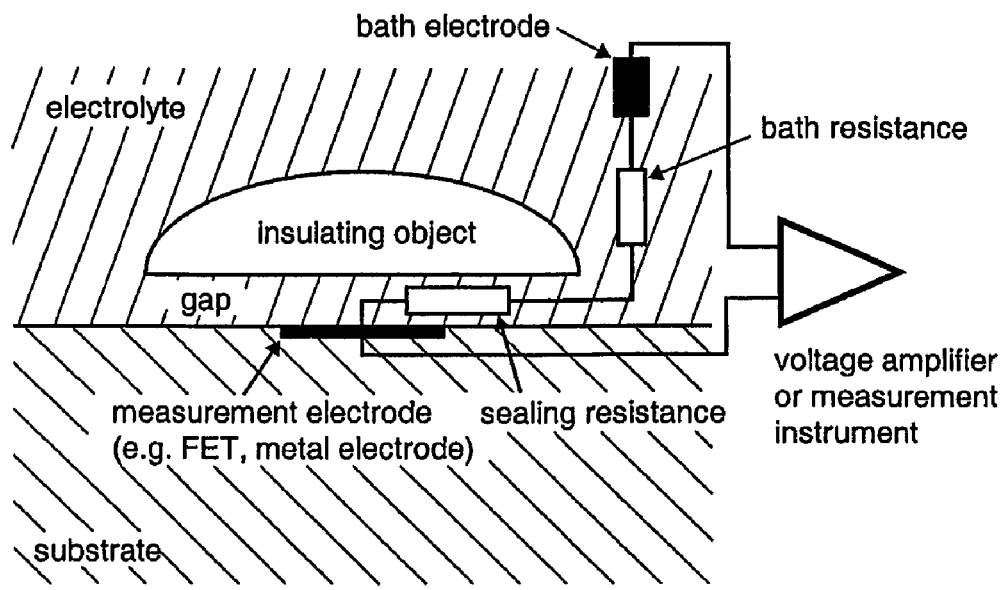

The invention relates to a method for determining the sealing of a substance on a support by determining the electrical noise.

The process of autonomous or actively initiated accumulation of a substance on a support can provide a large amount of information about the substance, about the support and about their interaction: in the case of actively initiated accumulation, for example by mechanical pressing of an object onto a support, the closeness of the contact depends on the contact pressure, on the elasticity of the object and on the roughness of the object and support. In the case of autonomous accumulation, for example of a lipid membrane onto a support, the sealing depends on the composition of the lipid membrane and on the chemical surface characteristics of the support.

One specific example of autonomous accumulation is cell adhesion. Cell adhesion denotes the adhesion of biological cells to one another, and of cells to substrates. This plays a major central role in the development of the adult organism. In all multiple cell living beings, the cell adhesion is controlled continuously during the development of the adult organism and during the formation of organs, in order to strengthen the cohesiveness of cell groups, or to reduce this. Furthermore, this controls the function of all epithelioid and endothelioid structures, for example of the intestine, of the bladder, of the blood vessels and of the blood/brain barrier.

The significance of cell adhesion will be explained using two specific examples: epithelia and metastases of cancer cells.

Epithelia consist of a single layer or multiple layer of epithelium cells. These line all of the internal cavities of the living beings and are used to bound the body from the environment. The most important factor is the permeability of the epithelia for water, ions, proteins and even for entire cells. The permeability is controlled by the lateral cohesion of the epithelium cells to one another. The formation of so-called "tight junctions" between the cells prevents the corresponding substances from diffusing from the side of the epithelium away from the body (the apical side) to the body's own side (the basal) side, or vice versa. The desired concentration differences are adjusted by regulation of the tight junctions and by means of active transport processes through the epithelium cells.

Cell adhesion is of interest in cancer research because the danger of a cancer tumor depends primarily on its capability to form metastases. Benign tumors admittedly grow but, provided that the cell group remains closed, the tumor can generally be completely removed surgically. In the case of malignant tumors, individual cells or small cell groups can become detached from the main tumor owing to changes in the cell adhesion, and can be distributed in the body, thus now rendering surgical removal virtually impossible. A method and an apparatus for investigation of cell adhesion is thus of interest for research into the mechanisms of tumor development and is of importance for the development of cancer pharmaceuticals, which could thus prevent cell detachment from the tumor or accumulation of cancer cells at other points in the body, and could thus reduce the danger of tumors.

In the prior art, methods are known in which the cell adhesion is determined by measuring the impedance by applying an alternating current and/or an alternating voltage.

An impedance Z means the frequency-dependent resistance of an electrically conductive material. The (complex-value) impedance is composed of the resistance and the reactance. The resistance corresponds to the real part Re(Z). The resistance is not frequency-dependent. The reactance corresponds to the frequency-dependent imaginary part of Z, which may be either a capacitive or an inductive reactance. The capacitive reactance is also referred to for simplicity in the following text as the capacitive resistance. The inductive reactance is of only minor importance for the present invention.

If the area of an electrode is reduced (with the surface characteristics otherwise remaining unchanged), the impedance of the electrode rises. The resistance is inversely proportional to the electrode area, and rises in a corresponding manner when the electrode area is reduced. The capacitive reactance is inversely proportional to the electrode capacitance and rises when the electrode area is reduced, since the capacitance component is reduced by the reduction in the area. In the case of electrodes which are in contact with an electrically conductive liquid, the resistance can in general be ignored. The capacitive reactance is dominant.

The existing method for characterizing cell adhesion by means of electrical measurements is electrode cell impedance sensing (ECIS, Giaever and Keese, Nature 366:591-592, 1993). In this case, cells are cultivated on metal electrodes. The impedance of the system comprising the electrode-cell bath is determined by applying a voltage to the electrode (with respect to a reference electrode in the bath) and by measuring the current flowing. The change in this impedance during culturing (typically a number of hours) allows deductions to be drawn about the growth, the adhesion, the propagation behavior, the mobility and the barrier effect of the cultivated cells.

In the ECIS method, the current flow across the boundary between the electrode and the electrolyte leads to electrochemical processes which are not precisely known. The effects of these electrochemical processes on the measurement results can accordingly be determined only with difficulty.

Owing to the current flow across the boundary between the electrode and the electrolyte, the impedance of the electrode in the ECIS method, with its real and imaginary parts, affects the measurement result. Owing to the rise in the impedance as the electrode becomes smaller, only electrodes with a specific minimum size, which cannot be undershot, may be used in the ECIS method. In practice, electrodes which have a diameter of at least 100 µm to 200 µm are used in the ECIS method. This size is larger than the size of an individual cell in the culture, which is adhering to a substrate. Because of the required minimum electrode size, the ECIS method does not allow measurement of the adhesion of an individual cell on a substrate. The ECIS method can be used, for example, to investigate layers of epithelium cells.

In the prior art, the impedance is also used to determine precipitations onto electrodes. U.S. Pat. No. 4,920,047 describes a method for determining an immunologically active substance by means of the change in the impedance of an electrode. An electrode is pretreated such that it binds either the immunologically active substance or else an enzyme. If there is no immunologically active substance in the sample, the bonded enzyme can form an insoluble precipitate on the electrode from suitable substrates. This precipitate changes the impedance of the electrode, thus allowing the concentration of the immunologically active substance to be determined. U.S. Pat. No. 4,920,047 determines the impedance by use of alternating current. Because of the current flowing across the boundary surface between the electrode and the electrolyte, the method described in U.S. Pat. No. 4,920,047 has the same disadvantages as the ECIS method described above (boundary-surface processes between the electrode and the electrolyte, relatively major influence of the impedance on the measurement result with relatively small electrodes).

Methods are known from the prior art which use voltage noise and current noise as measurement variables for determining the corrosion state of metal surfaces. Corrosion results in passivation/activation processes on the metal surface, which lead to fluctuations in the charge on the boundary surface between the metal and the electrolyte. The metal surface to be investigated thus varies continuously. The methods are designed for measuring the current and/or voltage noise on the metal surface to be investigated, with the surface being used as an electrode. The electrolyte remains unchanged during the measurement.

The expressions "electrochemical noise (ECN)" or "electrochemical noise analysis" are used in corrosion investigations. U.S. Pat. No. 6,611,151 describes a method for investigating coated metallic surfaces on the basis of the electrochemical noise. For this purpose, U.S. Pat. No. 6,611,151 uses an arrangement comprising three electrodes in an electrolyte. The first electrode is the material to be investigated, the second electrode is a reference electrode (for example Ag/AgCl), and the third electrode is a "witness" electrode composed of a more noble metal (for example platinum). The voltage noise between the reference electrode and the material to be investigated is measured, and the current noise between the "witness" electrode and the material is determined at the same time.

U.S. Pat. No. 5,888,374 discloses a method for determining corrosion processes by means of pitting. For this purpose, the electrochemical noise of the material to be investigated (for example corroding pipelines) is determined in an arrangement comprising three electrodes and an electrolyte in order to measure the current and voltage noise, with the material to be investigated representing one of these electrodes. Pitting results in a decrease in the spectral power density as the frequency rises in the region of very low frequencies ($10^{-4}$-$10^{-5}$ Hz). The noise of uniform corrosion is virtually independent of the frequency.

Vasilescu et al. (Electrochimica Acta, 1974, 19:181-186) describes the noise conductivity of electrolytes which has been determined by means of metal electrodes from the thermal noise, without using any external voltage. According to Vasilescu et al. (supra), the noise which is produced by the electrolyte corresponds to white noise. It is thus independent of the frequency. This approach was, however, not made use of later in order to develop methods for improved impedance measurement.

The object of the present invention is to provide a method for determining the sealing of a substance on a support, which entirely or partially overcomes the disadvantages described above of determining the sealing by impedance measurement by means of applying voltages and/or currents. The present invention is intended to overcome the disadvantage of existing methods that the electrodes used must have a specific minimum size in order to ensure that the electrode impedance does not interfere with the measurement.

In particular, the object of the invention is to provide an improved method for determining the adhesion of a substance on a support, for example of a biological substance such as a cell.

None of the methods from the prior art make use of the noise of the electrolyte as a measurement variable for determining the sealing and/or adhesion of a substance, in particular of a biological substance, on a support. The solution according to the invention is thus a method for determining the sealing of a substance on a support, comprising the steps:

(a) providing a substance on a support comprising at least one first electrode in contact with an electrically conductive liquid, wherein the substance entirely or partially covers the at least one first electrode, (b) determining the electrical noise of the impedance between the at least one first electrode and a second electrode, and (c) determining the sealing of the substance on the support from the electrical noise.

In one preferred embodiment, the method according to the invention further comprises the step:

(d) determining the adhesion of the substance on the support from the sealing of the substance on the support.

The noise of a variable is understood as meaning its fluctuations over time. The fluctuations are characterized in that they have a non-deterministic behavior, that is to say prediction of the signal over time is not possible. The fluctuations have a spontaneous origin, that is to say they do not originate from an external source, but originate from the system itself and cannot be avoided or suppressed.

All electrical impedance is noisy. In precise words, a voltage which fluctuates over time can be measured at the ends of an electrical impedance independently of external voltages and fields and is referred to, in the context of the present invention, as the noise voltage $V(t)$. The method according to the invention is based on the fact that the noise between two electrodes which are both in contact with an electrically conductive liquid becomes stronger when the impedance of the electrically conductive liquid rises. In view of the fact that an increase in noise correlates with a greater sealing, the measurement of the impedance of an electrically conductive liquid can be used for determining the sealing of a substance on a support.

FIG. 1 shows the schematic construction of an apparatus which is suitable for measuring the voltage noise using the method according to the invention. A voltage-sensitive electrode (measurement electrode), comprised by a support, is in contact with the electrically conductive liquid (electrolyte) which is located above it and in which a second electrode is located, which is used as a reference electrode.

Active or autonomous accumulation of an electrically insulating (or sufficiently poorly conductive) substance results in a gap between the electrode and the substance, with an electrical impedance, the sealing impedance. Example 1 according to the invention shows that a silicone bead which has been pressed onto the electrode surface leads to a considerable rise in the spontaneous time fluctuations (that is to say the noise) between the at least one first electrode and the second electrode. In this case, the silicone bead seals the entire electrode area from the surrounding electrically conductive liquid (see FIG. 2), and this leads to an increase in the impedance between the two electrodes. Example 2 according to the invention demonstrates the rise in the noise which is measured at electrodes which are sealed from the surrounding electrically conductive liquid by a living cell.

In the method according to the invention, the noise can be used in order to determine a different variable from this: the real part of the generally complex-value impedance between the electrodes. The impedance determined in this way may either itself be the desired variable or may be used on the basis of a suitable model of the sealing to determine other parameters, for example the width of the gap.

In the method according to the invention, the electrical noise of the impedance between the at least one first electrode comprised by a support and a second electrode can thus be used to determine the sealing of the substance, provided that the substance entirely or partially covers the at least one first electrode.

For the purposes of the present invention, "sealing of a substance on the support" describes, in a general form, the gap filled with electrically conductive liquid between the electrode, which is comprised by the support, and the substance. The "gap" comprises the space between the substance and the support and, in addition, all of the structures between the substance and the support as well as structures within the substance which can make a contribution to the sealing of the substance on the support. For example, the sealing of a living cell on a support may rise as a result of introduction of substances into the space between the cell and the support. A further example of structures which contribute to sealing but do not belong to the geometric space between the substance and the support are tight junctions, which connect living cells to one another.

The smaller and/or denser the gap, the greater is the contact between the substance and the support, and the greater is the sealing of the substance on the support. The greater the sealing, the greater is the impedance of the gap, in consequence. The impedance of the gap is thus also referred to as the sealing impedance in the following text. Without any substance on the support, no gap exists, and no sealing impedance either. It is possible to determine the sealing by means of the noise, with the sealing being the greater, the stronger the noise.

In the case of adhesion of individual cells in a normal culture medium, the sealing impedance is typically 500 kΩ to 10 MΩ, while it is 500 kΩ to 50 MΩ in the case of dense cell layers such as epithelium cells, and 1 MΩ to 1 GΩ in the case of materials which have been pressed on actively (such as the silicone bead in Example 1).

Depending on which parameters of the substance to be investigated, for example of a cell, of a cell group or of a cell membrane, are known, conclusions can be drawn from the sealing or sealing impedance on the support about the state and/or the change in the substance on the support.

The noise voltage V(t) of an (in general complex-value) impedance Z has the spectral power density $$S_V(f) = 4k_B T \cdot Re(Z) \quad \text{(I)},$$

wherein $k_B$ is Boltzmann's constant, T is the absolute temperature and Re(Z) is the real part of the impedance. This relationship applies in an entirely general form to electrical impedances, irrespective of the transport mechanism, of the nature of the charge carriers and of external voltages and fields. It is strictly valid when in thermodynamic equilibrium, and provides also in a large number of non-equilibrium states, in particular impedances through which a current is flowing, a good approximation. Voltage noise may be regarded as being caused by the Brown's molecular movement of charged particles (ions in the electrolyte, electrons in metals) or as a consequence of thermodynamic basic equations. The two analysis approaches are equivalent.

In the method according to the invention, the total impedance between the first and the second electrode is composed of four parts: the impedance of the first electrode, the impedance of the second electrode, the impedance of the electrically conductive liquid, and the sealing impedance.

Both the sealing impedance and the electrode impedances have complex values (both the real part and the imaginary part not equal to zero), with the real part being dominant in the case of the sealing impedance, and the imaginary part being dominant in the case of the electrodes.

In step (a) of the method according to the invention, the at least one first electrode is entirely or partially covered by the substance whose sealing and/or adhesion are/is intended to be determined. In one preferred embodiment, the at least one first electrode is at least 70% covered by the substance, more preferably at least 90% covered or even more preferably at least 95% covered, or most strongly preferably is entirely covered by the substance. If more than one first electrode is used, the electrodes may be entirely or partially covered with the substance independently of one another.

In step (b) of the method according to the invention, the electrical noise is determined between two electrodes. It is preferable for the determination of the noise in step (b) to be carried out essentially without any voltage or current being applied between the at least one first electrode and the second electrode (a measurement essentially without any voltage or current). The noise can thus be determined close to the thermodynamic equilibrium. Close to the thermodynamic equilibrium, the noise is determined by the impedance between the at least one first electrode and the second electrode in the electrically conductive liquid (electrolyte). This embodiment has the advantage that there is no need for apparatus for voltage and current application, for example for modulation of an electrode voltage and/or of an electrode current, as are required in impedance measurement methods from the prior art.

An essentially zero-voltage and zero-current measurement means, according to the invention, a measurement in which the at least one first electrode and the second electrode are each largely at the same potential as the surrounding electrically conductive liquid (zero-voltage state). Essentially no current thus flows via the boundary surfaces of the electrodes to the electrically conductive liquid (zero-current state). The essentially zero-voltage and zero-current measurement has the advantage that no electrochemical reactions occur at the boundary surface between the electrode and the electrolyte, because no current flows. In the method according to the invention, there is therefore no electrochemical noise as a possible source of interference with the measurements.

The electrical noise of an impedance can be determined as current noise and as voltage noise. In a further preferred embodiment of the invention, the electrical noise of the impedance is determined in step (b) as a noise voltage V(t).

The typical amplitude of the noise can be determined directly from the resistance value. The voltage noise of a resistance R has an RMS value in the frequency range $f_1$ to $f_2$ of:

$$V_{rms} = \sqrt{\int_{f_1}^{f_2} 4k_B T \cdot R \cdot df} = \sqrt{4k_B T \cdot R \cdot (f_2 - f_1)}. \quad \text{(II)}$$

The value Re(Z) of an impedance Z can also be substituted in the formula instead of R.

This means that the spectral power density and the RMS value depend only on the resistance Re(Z) of an impedance Z.

There is admittedly no well-defined peak-to-peak value for a noisy variable but, if an approximate peak-to-peak amplitude is required, the relationship:

$$V_{peak-peak} \approx 6.6 \cdot V_{rms} \quad \text{(III)}$$

can be used. The factor 6.6 is in this case based on the assumption that the peak-to-peak region is regarded as that region in which the signal moves during 99.9% of the time. This region thus corresponds to a Gaussian distribution of about ±3.2σ.

In a further preferred embodiment of the method according to the invention, the sealing of a substance is determined by determining the intensity of the noise in step (c). Stronger (weaker) noise is associated, for example, with an increase (reduction) in the amplitude. In this embodiment, the increase or decrease in the measured noise can be determined relative to the noise from a predetermined seal. The stronger or weaker sealing of the substance with respect to the predetermined seal can thus be determined. For this purpose, it is possible, for example, to define a threshold which must be overshot or undershot. It is preferable for the intensity of the noise to be determined in a predetermined frequency range $f_1$ to $f_2$.

In another preferred embodiment of the method according to the invention, the sealing of the substance on the support is determined in step (c) from the peak-to-peak amplitude of the noise voltage in a predetermined frequency range $f_1$ to $f_2$. In this case, it is preferable to calculate the peak-to-peak amplitude using:

$$V_{peak-peak} \approx 6.6 \cdot V_{rms} \quad \text{(III)}.$$

Because of the proportionality, any desired factor other than 6.6 may be used. In particular, it is also possible to use the $V_{rms}$ value directly as a measure of the peak-to-peak amplitude.

In yet another preferred embodiment of the method according to the invention, the sealing of the substance on the support is determined in step (c) from the amplitude of the noise voltage in a predetermined frequency range $f_1$ to $f_2$, with the amplitude being characterized by the voltage range in which the electrical noise voltage moves for up to 95%, preferably for up to 99%, and more preferably for up to 99.9% of a predetermined time period.

In a further preferred embodiment of the method according to the invention, the sealing of the substance on the support is determined in step (c) from the amplitude of the noise voltage in a predetermined frequency range $f_1$ to $f_2$, with the amplitude of the noise voltage being characterized by ±3.2σ. σ is the standard deviation of the distribution of the individual values of the noise voltage measured over a predetermined time. It is likewise possible to use any desired factor other than 3.2 and/or $\sigma^2$ instead of σ. In particular, it is also possible to use a directly as a measure for the amplitude.

A person skilled in the art can obtain a very good approximation of the electrical characteristics of substances on the supports by means of equivalent circuits which describe the components involved by means of passive and active electrical components. Passive electrical components may be resistances/conductances and/or capacitances. Active electrical components may be voltage sources (for example Nernst potentials across membranes) and/or rectifiers (for example ion channels).

A person skilled in the art can equally well produce equivalent circuits for non-biological and biological substances which are provided on a support according to step (a) of the method according to the invention.

A summarizing description of the equivalent circuits of living cells can be found, for example, in Hille, B., "Ionic Channels of Excitable Membranes", Sinauer Associates Inc., Sunderland, Mass., 1991.

Using an equivalent circuit of the arrangement comprising the at least one first electrode, the second electrode in the electrically conductive liquid and the substance, a person skilled in the art can use the sealing impedance to determine the characteristic variables which are a measure for the adhesion of the substance on the support. One measure for the adhesion may be the resistance $r_s$ of the space between the substance and the support, or the sealing impedance which is defined by the sealing of the substance, the width of the gap between the cell and the substance, and/or the layer permeability (for example the impedance of tight junctions) (see above).

The following three examples relate to biological substances, which lead to characteristic sealing impedances. Since the method according to the invention preferably operates without any current and voltage (see above), only the passive components are shown in the equivalent circuits in FIGS. 3 to 5, for simplicity reasons.

In the case of a single cell of a sensor (FIG. 3), the sealing impedance is formed from the resistance $r_s$, the leakage conductances $g_{l,f}$ and $g_{l,a}$ and the membrane capacitances $c_{m,f}$ and $c_{m,a}$, in each case for the free and adhered cell membrane, respectively. The leakage conductances and the membrane capacitances are generally known quite accurately, so that the resistance $r_s$ can be determined using the method that is known to a person skilled in the art for circuit calculation with the aid of the known parameters from the sealing impedance. This is governed predominantly by the width of the gap between the cell and the support, and thus provides information about the cell-support adhesion and about changes to it, for example when active substances are added.

In the case of a layer composed of epithelium cells (FIG. 4), so-called "tight junctions" are formed between the cells, and act as a diffusion barrier for water and ions, and thus have a high impedance. Individual epithelium cells in the layer can be described in the same way as individual cells from FIG. 3 or by the impedances of the free ($Z_a$) and adhered ($Z_b$) cell membrane, respectively. The resistance $R_{tj}$ of the tight junctions is one of the most important parameters of an epithelium structure and thus directly provides information about its function. On the basis of the given parameters, a person skilled in the art can determine the resistance of the tight junctions $R_{tj}$ or their impedance from the sealing impedance using known methods for circuit calculation. Any change to the tight junctions, for example when an active substance is added, can be used as a test for the effectiveness of the active substance.

In the case of a lipid double membrane (FIG. 5), also referred to as a "supported lipid bilayer", the sealing impedance is formed from the resistance $r_s$ as well as from the capacitance $c_m$ and the leakage conductance $g_l$ of the lipid membrane. On the basis of the given parameters, a person skilled in the art can determine the resistance $r_s$ or the corresponding impedance from the sealing impedance, using known methods for circuit calculation. A lipid membrane represents a simple model system for the membranes of biological cells. Membrane proteins and ion channels can thus be incorporated and their reaction on messenger substances can be investigated when this influences the conductance of the membrane. Biosensors, in particular, can thus be constructed specifically using ion channels.

Figure 3:
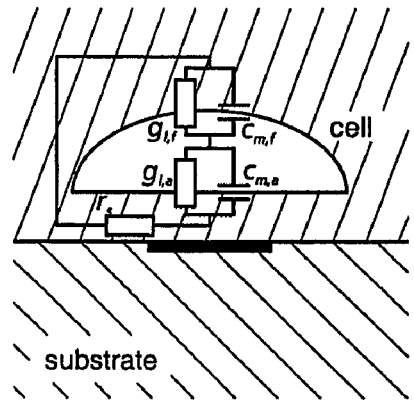
Figure 4:
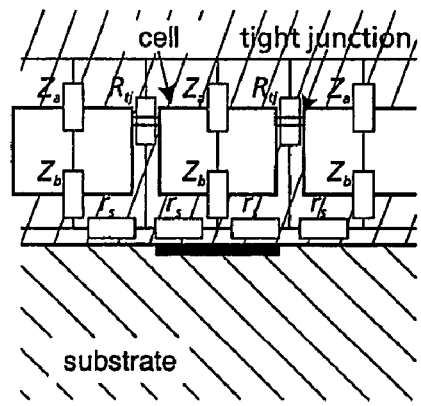
Figure 5:
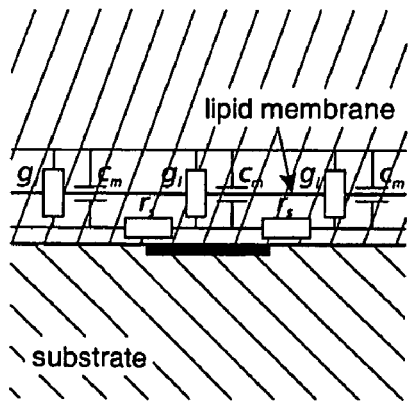

In the equivalent circuits shown in FIGS. 3 to 5, the resistance/the impedance in the electrically conductive liquid (electrolyte) outside the gap is not shown, for the sake of clarity.

The measured noise is composed of the noise of the measurement apparatus and the noise of the sealing impedance of the substance to be investigated. The noise of the measurement apparatus can be eliminated, if required, by comparative measurements without any substance on the support.

In a further preferred embodiment, the method according to the invention comprises, in step (c):
- (c1) determining the impedance, preferably the real part of the impedance, from the noise voltage, and
- (c2) determining the sealing of the substance on the support from the impedance, preferably from the real part of the impedance.

More preferably, in step (c1) of this embodiment, the impedance, preferably the real part of the impedance, is determined from the time-dependent noise voltage.

The real part of the impedance can be determined from the spectral power density $S_V(f)$ using, for example:

$$S_V(f) = 4k_B T \cdot Re(Z) \tag{IV}$$

In another preferred embodiment, the method according to the invention comprises in step (c):
- (c1) determining the spectral power density from the noise voltage, and
- (c2) determining the sealing of the substance on the support from the spectral power density.

More preferably, in step (c1) of this embodiment, the spectral power density is determined from the time-dependent noise voltage V(t).

In this embodiment, the highly suitable spectral power density is used to describe electrical noise. For a given time-dependent variable a(t), the spectral power density (also referred to as the "power density spectrum" or simply the "power density") $S_a(f)$ of this variable a(t) can be defined as:

$$S_a(f) := \lim_{T \to \infty} \frac{1}{2T} \left| \int_{-T}^{T} e^{i2\pi f t} a(t) dt \right|^2 \tag{V}$$

The spectral power density of the noise of the total impedance is given by:

$$S_V(f) = 4kT \cdot Re(Z_{total})$$

$$= 4kT \cdot Re(Z_{first\ electrode} + Z_{liquid} + Z_{seal} + Z_{second\ electrode})$$

$$= 4kT \cdot (Re(Z_{first\ electrode}) + Re(Z_{liquid}) + Re(Z_{seal}) + Re(Z_{second\ electrode})) \tag{VI}$$

The noise and its measurement are thus advantageously not influenced by any imaginary impedance (that is to say without any real part), as occurs, for example, with purely capacitive electrodes. Any imaginary impedance is not included in the measurement, and therefore does not interfere with it. Capacitive electrodes, whose impedance is virtually exclusively imaginary, can thus be reduced in size for use in the method according to the invention (as far as the limits of what is technically feasible), since the increase in the imaginary impedance associated with the reduction in size does not interfere with the measurement.

The mean value over time:

$$\bar{a} := \lim_{T \to \infty} \frac{1}{2T} \int_{-T}^{T} a(t) dt \tag{VII}$$

is preferably ignored or is set to zero for determination of the spectral power density by splitting the general function a(t) into its mean value over time and its fluctuation, and by using only the fluctuation in the treatment of the noise. If the mean value over time is not zero, this appears in the spectral power density as a delta function at the frequency zero. Ignoring this or setting it to zero makes it possible to avoid the mathematically complex treatment of a delta function such as this.

In this embodiment, it is preferable, in step (c2), to determine the sealing from the integral of the spectral power density over a predetermined frequency range $f_1$ to $f_2$ and/or from the square root of the integral of the spectral power density over a predetermined frequency range $f_1$ to $f_2$:

$$V_{rms} := \sqrt{\int_{f_1}^{f_2} S_V(f) df} \tag{VIII}$$

The square root of the integral of the spectral power density over a predetermined frequency range $f_1$ to $f_2$ is also referred to as the $V_{rms}$ value (see equations (I) and (II)). It is preferable for the $V_{rms}$ value to be determined by filtering a predetermined frequency range $f_1$ to $f_2$ out of the noise voltage signal, for example by using a bandpass filter to select the frequency range of interest, and by then forming the root mean square value of the square of the voltage in a predetermined time interval.

In a further preferred embodiment, the method according to the invention comprises, in step (c):
- (c1) determining the autocorrelation function from the noise voltage, and
- (c2) determining the sealing from the autocorrelation function obtained in step (c1).

In this embodiment of the present invention, the so-called autocorrelation function is used for noise analysis, being defined for a time-dependent variable a(t) as:

$$p(\tau) := \lim_{T \to \infty} \frac{1}{2T} \int_{-T}^{T} a(t) a(t+\tau) dt \tag{IX}$$

which is a different representation of the spectral power density. The spectral power density is the Fourier transform of the autocorrelation function (and vice versa). It is more preferable to determine the autocorrelation function from the time-dependent noise voltage V(t) in step (c1).

In the method according to the invention, the measurements may have any desired length. Typically, the noise of the impedance is analyzed over times from a few milliseconds to several minutes. The measurement time is preferably 10 ms to 1000 s, more preferably 1 to 300 s, even more preferably 5 to 60 s, and most preferably 10 to 30 s.

Example 1 shows that the method according to the invention makes it possible to observe changes in the impedance in real time. The example shows an impedance rise within a few milliseconds and a fall which is just as fast, and which was demonstrated by an increase or reduction in the noise at a corresponding rate.

In a further preferred embodiment, the method according to the invention thus detects rapid impedance changes. In particular, the method according to the invention detects impedance changes with a resolution of at most 1000 ms, more preferably at most 100 ms, even more preferably at most 10 ms, and most preferably at most 1 ms.

In yet another preferred embodiment, the detection of rapid impedance changes is combined with a parallel measurement at a plurality of electrodes, for example as described below.

The power density spectrum obtained from the noise voltage extends over a wide frequency range and, on the basis of its profile, provides more information than the measurement of the impedance at a single frequency. In the method according to the invention, all frequencies can advantageously be investigated in parallel, using the spectral power density of the noise voltage.

The frequency range over which the noise voltage can be measured in the present method is restricted only by the characteristics of the apparatuses used. In particular, the characteristics of the measurement apparatus govern the maximum possible time resolution of the method according to the invention.

In practice, the spectral power density may be dominated by the electrode noise both in the low-frequency range (below about 300 Hz) and in the high-frequency range (above about 30 000 Hz). Additional noise, which is caused by the sealing of a substance on a support, is evident in the range from about 300 to about 30 000 Hz. Thus, in the method according to the invention, the noise is determined in the frequency range $f_1$ to $f_2$ preferably from about 100 Hz to about 100 kHz, or in a subregion of this, more preferably from about 300 Hz to about 30 kHz, or in a subregion of this, and even more preferably from about 2 kHz to about 10 kHz, or in a subregion of this.

The integral of the spectral power density over the frequency range $f_1$ to $f_2$ from about 2 to about 10 kHz may correlate very well with the coverage resulting from the sealing substance on the support. The integral of the spectral power density is thus preferably determined over the limits $f_1$ to $f_2$ from about 100 Hz to about 100 kHz or a subregion of it, more preferably from about 300 Hz to about 30 kHz or a subregion of it, and even more preferably from about 2 kHz to about 10 kHz or a subregion of this.

The steps (b) and (c) of the method according to the invention can be carried out with a time interval between them.

In step (d) of one preferred embodiment of the method according to the invention, the adhesion of the substance on the support is determined from the sealing of the substance on the support. The adhesion of a substance may be determined in particular for substances which are capable of autonomous accumulation on a support. Substances which are capable of autonomous accumulation are in particular biological substances such as cells, cell layers, lipid membranes etc, as described below.

In general, the adhesion of an autonomously accumulating substance rises as the sealing increases.

The parameters described above, which may be a measure for the sealing, may thus also be a measure for the adhesion of the substance on the support.

Suitable analogue electronic apparatuses which are known to a person skilled in the art (filters, apparatuses for integration, Fourier transformation, determination of $V_{rms}$, etc.) may be used to carry out step (b), step (c) and/or, if appropriate, step (d) of the method according to the invention. Step (b) and/or step (c) of the method according to the invention can also be carried out with a combination of a computer or computers and an analogue apparatus or analogue apparatuses. The computer(s) comprise(s) a program code which is suitable for carrying out and/or controlling the method steps. A person skilled in the art can create a suitable program code on the basis of the details in this description.

The substance to be investigated using the method according to the invention may be a biological substance, in particular a cell, a cell group (for example a tissue), a cell culture or a membrane. Any cell, any cell group, any cell culture or any membrane may be investigated which can be applied to a support material which comprises one or more electrodes, so that the substance entirely or partially covers at least one electrode.

The adhesion of a cell, of a cell group or of a cell culture is preferably determined, that is to say the cell adhesion is preferably determined.

The cell group or the cell culture preferably forms a single-cell layer, in particular a confluent single-cell layer, or a multiple-cell layer. One example of a suitable cell line is the well-established MDCK epithelium cell line. These are cells from dog kidneys (the letters CK are short for "canine kidney"). Various lines, which differ in particular in the sealing of the cell layer that is formed, are known from MDCK. All of these lines are suitable for the method according to the invention.

In a further preferred embodiment, the cell, the cell culture or the cell group is cultivated on the support.

The substance may likewise be a synthetic lipid layer (lipid double membrane), which may contain proteins.

The support for the substance is produced from a material which is suitable for embedding at least one first and, where appropriate, the second electrode. The substance is in this case an electrical insulator. In one preferred embodiment, the support is formed from a semiconductor, for example silicon, GaAs or GaN (in particular if transistors are used as the first electrode(s)), glass, a polymer, sapphire and/or composite materials composed of these materials. Support materials such as these are known to those skilled in the art.

In a further preferred embodiment, the support is suitable for holding biological materials, that is to say the support is bio-compatible. For this purpose, its surface characteristics are of particular importance. In one particularly preferred embodiment, the surface is modified by means of a suitable coating in such a way as to promote the application, growth or the adhesion of cells on the coating. Preferred coatings are composed of polypeptides such as laminin, polylysin, collagen and/or fibronectin. A thin coating such as polylysin and/or collagen makes it easier to grow and cultivate cells and/or cell layers on the support, but does not significantly change the electrical characteristics of the electrode. Bio-compatible surfaces and coating materials are known to those skilled in the art.

In the method according to the invention, it is preferably to use electrodes whose electrical characteristics do not change significantly during the measurement time period.

In general, the composition of the conductive liquid in the gap between the substance and the at least one first electrode corresponds essentially to the composition of the remaining conductive liquid during the measurement period. However, it is also possible to form a concentration gradient between the apical side and the basal side, for example when epithelium cells are being grown on the support, that is to say specific substances, in particular ions, may be enriched or depleted in the gap between the cell layer and the substrate, thus influencing the resistance $r_s$, and hence the sealing impedance. An increase in concentration caused by the cells can thus also be observed using the method according to the invention.

The electrode impedance is the impedance which is created in the electrolyte during the coupling of the charge transports which are based on electron conduction (in metals) or electron/hole conduction (in semiconductors) to charge transport based on ion conduction. This depends on the physical form (for example bare metal electrode, silver/silver-chloride electrode, field-effect transistor), and the size of the electrodes.

In the method according to the invention, the at least one first electrode comprised by a support may be a voltage-sensitive electrode. The way in which a voltage-sensitive electrode such as this is formed is known to those skilled in the art. In one preferred embodiment, the at least one first electrode is a transistor, in particular a field-effect transistor, or a metal electrode. Preferred materials for a metal electrode according to the invention are selected from noble metals such as platinum, gold, titanium and alloys thereof, indium-tin oxide (ITO), and semiconductors such as silicon, germanium, GaAs, GaN and alloys thereof.

The contact between the at least one first electrode and the substance may be created directly or by means of a thin electrical insulator, for example silicon dioxide.

In the case of the electrodes according to the invention, the imaginary part determines the impedance, and the real part of the impedance can in general be ignored. Any reduction in the electrode area thus results only in the rise in the imaginary impedance (see above). In the method according to the invention and the apparatus according to the invention (see below), the imaginary impedance of the at least one first electrode does not influence the measurement of the noise voltage, that is to say small electrodes do not present any problem for the method according to the invention. At low noise frequencies, at which the imaginary part of the impedance is higher than the imaginary part of the impedance at higher frequencies, this characteristic of the method according to the invention and of the apparatus according to the invention is particularly advantageously noticeable.

The method according to the invention is accordingly suitable for working with small sensor areas. A lower limit for the electrode size is governed only by the technical capabilities for production of electrodes comprised by a support. In particular, it is advantageously possible to use electrodes whose diameters are less than the diameter of cells (typically 10 to 20 µm) which are cultivated on the support, or for which the area that is covered by the electrode on the support is smaller than the area covered by the cell.

It is preferable for the at least one first electrode, in particular a round electrode, to have a diameter of at least 1 µm, more preferably of at least 2 µm, and even more preferably of at least 5 µm. It is also preferable for the at least one first electrode to have a diameter of at most 100 µm, more preferably of at most 30 µm, and most preferably of at most 10 µm.

The electrode may have any desired shape, for example being round, quadrilateral, etc. The shape of the electrode is restricted only by the technical capabilities for production of electrodes comprised by a support. For example, transistors may be produced with rectangular gate areas, with the gate length (in the current flow direction) typically being considerably greater than the gate width. The at least one first electrode preferably covers a support area of at least 1 µm$^2$, more preferably of at least 5 µm$^2$, and even more preferably of at least 25 µm$^2$. The at least one first electrode preferably covers a support area of at most 10 000 µm$^2$, more preferably of at most 1000 µm$^2$, and even more preferably of at most 100 µm$^2$.

It is also preferable for the support to comprise a plurality of first electrodes, so that the sealing impedance of the substance which is applied to the support can be measured at a plurality of positions. Since very small electrodes can advantageously be used, very high electrode densities are possible. For example, the electrodes may be arranged linearly (see examples) or in the form of a two-dimensional array. The distance between the electrodes may be chosen as required. A distance of at most 200 µm is preferable, more preferably at most 50 µm, even more preferably at most 10 µm, and most preferably at most 2 µm. The support preferably comprises at least 5 electrodes, more preferably at least 10, even more preferably at least 50, and most preferably at least 100 electrodes. The support preferably comprises a maximum of 20 000 electrodes, more preferably a maximum of 5000, even more preferably a maximum of 1000, and most preferably a maximum of 200 electrodes.

The plurality of electrodes on which measurements are carried out in parallel also make it possible to observe changes in the substance, for example migration, growth and/or division processes of cells on the support. For instance, Example 2 shows a measurement which uses the high spatial resolution of an arrangement of the first electrodes in order to create a sealing profile of a single cell on a support.

In the method according to the invention, any electrode which is suitable for use as a reference electrode in an electrically conductive liquid may be used as the second electrode. In particular, the second electrode may be larger than the at least one first electrode. The second electrode may also be provided in the same way as the at least one first electrode, or else may be a silver electrode, in particular an Ag/AgCl electrode.

It is preferable for the at least one first electrode and the second electrode to be provided such that their impedance is negligible in comparison to the sealing impedance.

The conductivity of the electrically conductive liquid may vary within wide limits. The electrically conductive liquid may be an aqueous saline solution, in particular a cell culture medium or a saline solution which is suitable for holding cells. Suitable cell culture media and saline solutions are known to those skilled in the art.

The entire range from liquids with very low conductivity (such as deionised water) to liquids with very high conductivity (for example a saturated aqueous saline solution) may be used for non-biological applications. For a given gap geometry, the sealing impedance can be brought to a range that can be measured well by a suitable choice of the conductivity of the electrically conductive liquid.

It is preferable for the impedance of the electrically conductive liquid to be negligible in comparison to the sealing impedance.

The impedance of the first electrode, of the second electrode and/or of the electrically conductive liquid is negligible when it is at most 10%, preferably at most 1%, more preferably at most 0.1%, and most preferably at most 0.01% of the sealing impedance. If required, the impedance of the first electrode, of the second electrode and/or of the electrically conductive liquid can be determined separately by means of a check measurement without any substance on the support.

The sealing impedance is linked via the gap width and sealing geometry to the conductivity of the electrically conductive liquid. The gap width can thus be calculated, for example, from the known conductivity of the electrically conductive liquid and the measured sealing impedance.

The impedance of the electrically conductive liquid is the impedance which results from the finite conductivity of the electrolyte between the first and the second electrode, and is proportional to the conductivity of the electrolyte. The proportionality factor is governed solely by the geometry of the arrangement comprising the first electrode, the second electrode and the electrically conductive liquid. If the first electrode is small in comparison to the dimensions of the second electrode and of the bath containing the electrically conductive liquid, the proportionality factor for the electrically conductive liquid is governed by the geometry of the first electrode. For example, the impedance of an electrolyte with a circular planar electrode whose diameter is d and which is located with one side in contact with an electrolyte of infinite extent (half-space) is:

$$R_{Bath} = \frac{\rho}{2d}. \qquad (X)$$

In this case, ρ is the resistivity of the electrolyte and is quoted in ohm.cm. This value is also a good approximation for the square electrodes that are frequently used in practice, provided that the square electrode is converted to a circular electrode with the same surface area.

The sealing impedance depends on the width of the gap between the support and the substance on the support. The gap width may be a few nanometers (for example in the case of mechanically supporting contact between very smooth surfaces or in the case of an attachment of a lipid membrane). The gap width for active contact between the substance and the support (for example in Example 1) is preferably 0 to about 5 nm. The gap width for a lipid membrane on a support (for example in Example 4) is preferably 0 to about 10 nm. In the case of biological cells which are adhered to the electrode, the gap width may be in the region of about 50 nm. If the substance is a biological cell, a cell layer, a cell culture or a cell group, the gap width is preferably at least about 20 to about 200 nm, more preferably at least about 30 to about 100 nm.

It is preferable for the gap to be small in comparison to the diameter of the at least one first electrode. If the gap width and the diameter of the electrode were to be of a comparable size, there would not be a significant increase in the sealing impedance.

Applications for the method according to the invention include, for example: the investigation of spontaneous cell adhesion on a substrate, the influence of specific coatings on the adhesion, the development of the adhesion with increasing culture duration, the influence of added pharmaceuticals to the adhesion. One major advantage is that individual cells can be investigated, because of the small electrode or transistor size. The method does not result in an averaged signal over a large number of cells, and instead it is possible to investigate the accumulation and dissolution processes of a single cell, which are typically initiated by quite specific signal paths within the cell. Since the cell reacts as an entity, and different cells, however, act on this signal path at different times, information is lost when averaging is carried out over a large number of cells.

A further subject matter of the present invention is an apparatus for carrying out the method according to the invention as described above, comprising:
(i) a support for holding a substance, comprising at least one first electrode in contact with an electrically conductive liquid,
(ii) means for measuring the electrical noise of the impedance between the at least one first electrode and a second electrode, and
(iii) means for determining the sealing of the substance on the support from the electrical noise.

In one preferred embodiment, the apparatus according to the invention also comprises:
(iv) means for determining the adhesion of the substance on the support from the sealing of the substance on the support.

The support according to (i) may be a support as described above for the method according to the invention. It is preferable for the support to comprise a plurality of first electrodes.

The means for measuring the noise according to (ii) may comprise means for carrying out the step (b) of the method according to the invention, for example as described above. An apparatus is preferred which allows a zero-current and zero-voltage measurement to be carried out, as described above. This apparatus is preferably controlled by a computer and comprises means for storing the results of the measurement of the noise.

The means for determining the sealing on the support from the electrical noise according to (iii) may comprise means for carrying out the step (c) of the method according to the invention, for example as described above.

It is preferable for the means according to (iii) to be provided in the form of a program product which can be run on a computer.

The means for determining the sealing on the support from the electrical noise according to (iii) preferably comprises means for
(iii1) determining the spectral power density from the noise voltage, and
(iii2) determining the sealing of the substance on the support from the spectral power density.

(iii1) preferably comprises means with which the spectral power density can be determined from the time-dependent noise voltage.

(iii2) preferably comprises means in order to allow the sealing to be determined from the integral of the spectral power density over the frequency and/or from the square root of the integral of the spectral power density over the frequency.

It is furthermore preferable for the apparatus according to the invention to comprise means with which the noise can be determined preferably in the range from about 100 Hz to about 100 kHz or in a subregion thereof, more preferably from about 300 Hz to about 30 kHz or in a subregion thereof, and most preferably between about 2 kHz and about 10 kHz or in a subregion thereof.

The apparatus according to the invention can be designed such that the means (ii) and (iii) are spatially separated from one another, and/or can be used with a time interval between them.

In one preferred embodiment, the means according to (iv) may comprise means for carrying out the step (d) of one preferred embodiment of the method according to the invention, for example as described above.

Known apparatuses are not suitable for carrying out the method according to the invention as described above. An apparatus according to the invention can be obtained by combining known apparatuses, for example for carrying out the established ECIS method, with suitable supplementary apparatuses and/or software products, which may promote rapid market implementation and acceptance of the method according to the invention. In particular, supports comprising electrodes can be used to culture biological systems which have already been used for the ECIS method in the method(s) according to the invention or the apparatus according to the invention, provided that smaller electrodes are not required for the intended purpose.

A further subject matter of the present invention is a method for identifying a compound, which modulates the sealing of a substance on a support, comprising the steps:
(I) determining the sealing of the substance on a support using the method according to the invention as described above and/or using the apparatus according to the invention as described above, in the absence of the compound to be investigated,
(II) determining the sealing of the substance on a support using the method according to the invention as described above and/or using the apparatus according to the invention as described above in the presence of the compound to be investigated, and (III) selecting a compound which modulates the sealing of the substance on the support in a predetermined manner.

Furthermore, the invention relates to a method for identifying a compound which modulates the adhesion of a substance on a support, comprising the steps:

(1) determining the adhesion of the substance on a support using the method according to the invention as described above and/or using the apparatus according to the invention as described above in the absence of the compound to be investigated, (2) determining the adhesion of the substance on a support using the method according to the invention as described above and/or using the apparatus according to the invention as described above in the presence of the compound to be investigated, and (3) selecting a compound which modulates the adhesion of the substance on the support in a predetermined manner.

"Modulated in a predetermined manner" means that a prior determination is made as to whether the sealing and/or the adhesion should be increased or reduced in comparison to the check value (in the absence of the compound to be investigated), or should differ from the check value. In this case, a threshold may be predetermined which must be overshot or undershot in order to select a compound according to step (III) or (3).

The substance which is used in the identification method is preferably a biological substance.

If, by way of example, the substance is a confluent layer composed of cells which are joined to one another by means of tight junctions, the identification method can be used to find active substances which interact with the cells and/or the tight junctions and vary the impedance of the tight junctions. Active substances which, for example, increase the impedance of the tight junctions may be used for cancer therapy since, by stabilization of the tight junctions, they could prevent cell detachment from a tumor (and thus the formation of metastases), thus making it possible to reduce the danger of tumors.

If, for example, the substance is a single cell, then the identification method according to the invention can be used to identify active substances which influence the sealing and/or adhesion of the cell on the support.

If, for example, the substance is a lipid double membrane, then proteins, for example ion channels and/or ion pumps, can be incorporated in this membrane. The identification method according to the invention can be used to identify substances which influence the conductivity of the lipid membrane by the substances influencing the conductivity of the incorporated proteins, in particular of incorporated ion channels and/or ion pumps.

Furthermore, the identification method according to the invention can be used for diagnosis by investigating samples from clinical isolates, for example isolates from tumors, for their capability for sealing and/or adhesion on supports. For example, the sealing and/or the adhesion of cultivated tumor tissue may thus allow a quantitative statement to be made about whether the tumor is benign or malignant. The higher the sealing and/or adhesion, the lower the danger of the tumor can be assessed as being, since the tendency for detachment of cells and cell groups from the tumor is less. The probability of metastases is thus less.

The applications as described above likewise allow the identification method according to the invention to be used to investigate tumor creation mechanisms.

In a further preferred embodiment, the identification method according to the invention is carried out using the high-throughput format.

A further subject matter according to the invention is a computer program product which, when it is loaded into the memory of a suitable computer, where appropriate together with suitable hardware, is suitable for carrying out the method according to the invention as described above.

A further subject matter according to the invention is a biosensor, comprising a support comprising at least one first electrode and a lipid double membrane which entirely or partially covers the at least one first electrode. The lipid double membrane may contain proteins, for example ion channels. These ion channels may be ligand-controlled, so that the sealing impedance of the lipid double membrane is modulated by the presence of ligands which are present in a sample which is brought into contact with the biosensor. Suitable lipid double membranes, ion channels and ligands are known to those skilled in the art. Suitable supports and electrodes are described in conjunction with the method according to the invention. The modulation of the sealing impedance can be determined by means of its noise, as described above.

The invention will be explained in more detail by means of the following figures and examples.

FIG. 1 shows the measurement principle according to the invention. The sealing/adhesion can be determined by measuring the noise voltage as the impedance Z between the measurement electrode and an electrode in the electrically conductive liquid.

Figure 2:
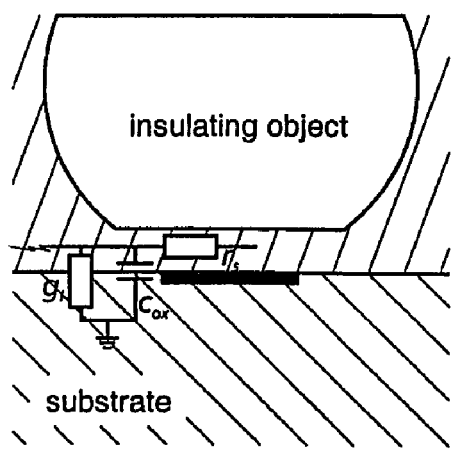

FIG. 2: sealing by means of a perfectly insulating object, schematic.

FIG. 3: cell on an electrode. The cell membrane has a high electrical impedance, and thus seals the electrode.

FIG. 4: a layer cultivated on the substrate composed of epithelium cells seals the electrode. The sealing of the overall layer is governed essentially by the resistance/the impedance of the "tight junctions" between the cells.

FIG. 5: lipid membrane on a solid substrate ("supported lipid bilayer"). Trans-membrane proteins, in particular ion channels, may be incorporated in the membrane and influence the sealing impedance.

Figure 6:
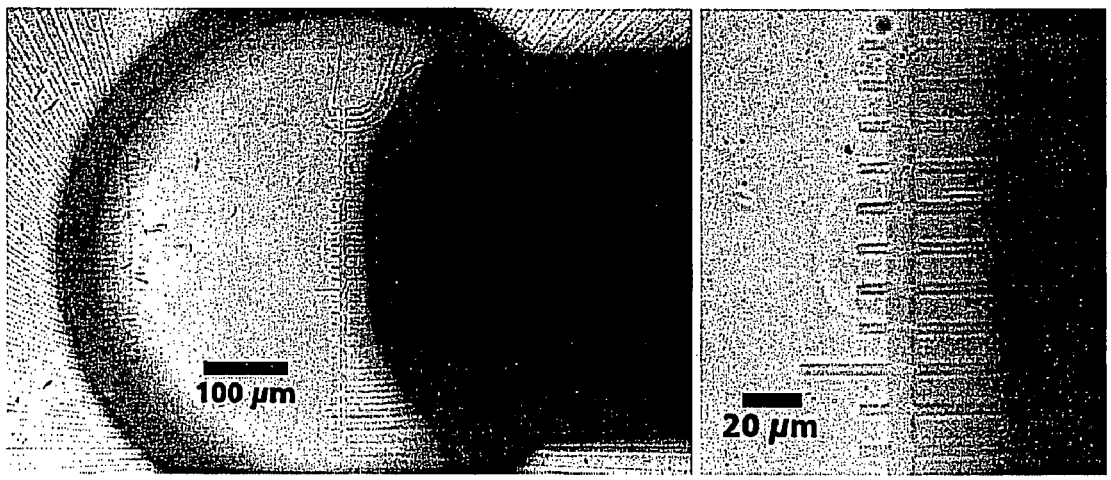

FIG. 6: silicone bead in contact with a linear transistor array. On the right, an enlarged view in which the contact area can be seen as a slightly darker spot with a light edge. This extends over a total of 4 transistors, and has a diameter of about 50 µm.

Figure 7:
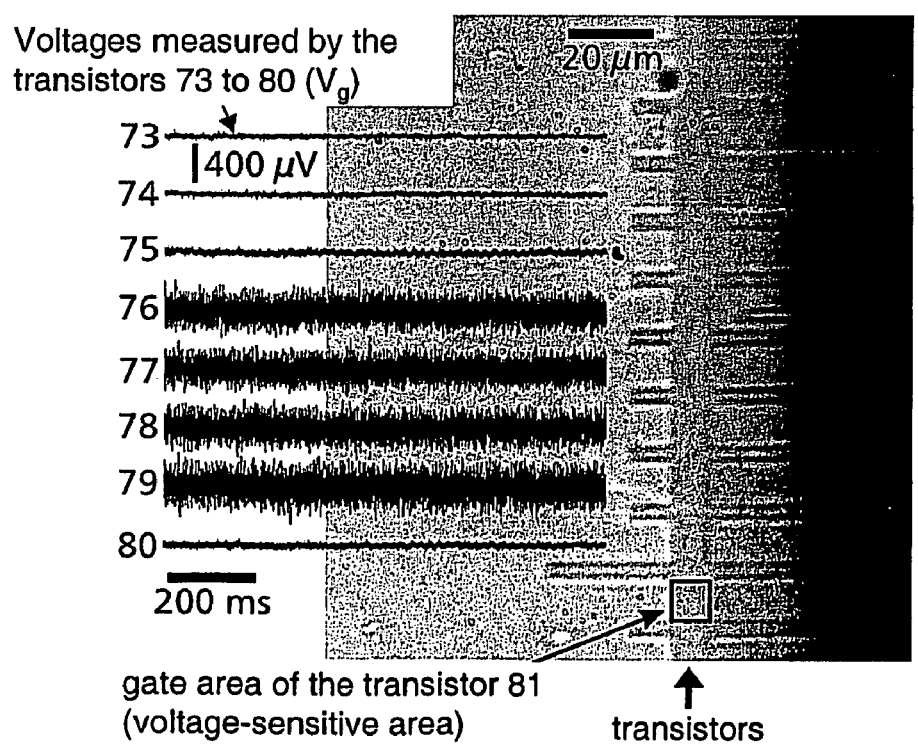

FIG. 7: gate voltages of the transistors in the contact area. FETs 76 to 79 which are in contact with the silicone bead have considerably increased noise. The gate area of FET 81 is shown with a black boundary, in order to assist understanding. This has a size of about 6×7 µm$^2$. The gate area is the effective, voltage-sensitive area of a field-effect transistor and corresponds to the electrode area in the case of conventional metal electrodes.

Figure 8:
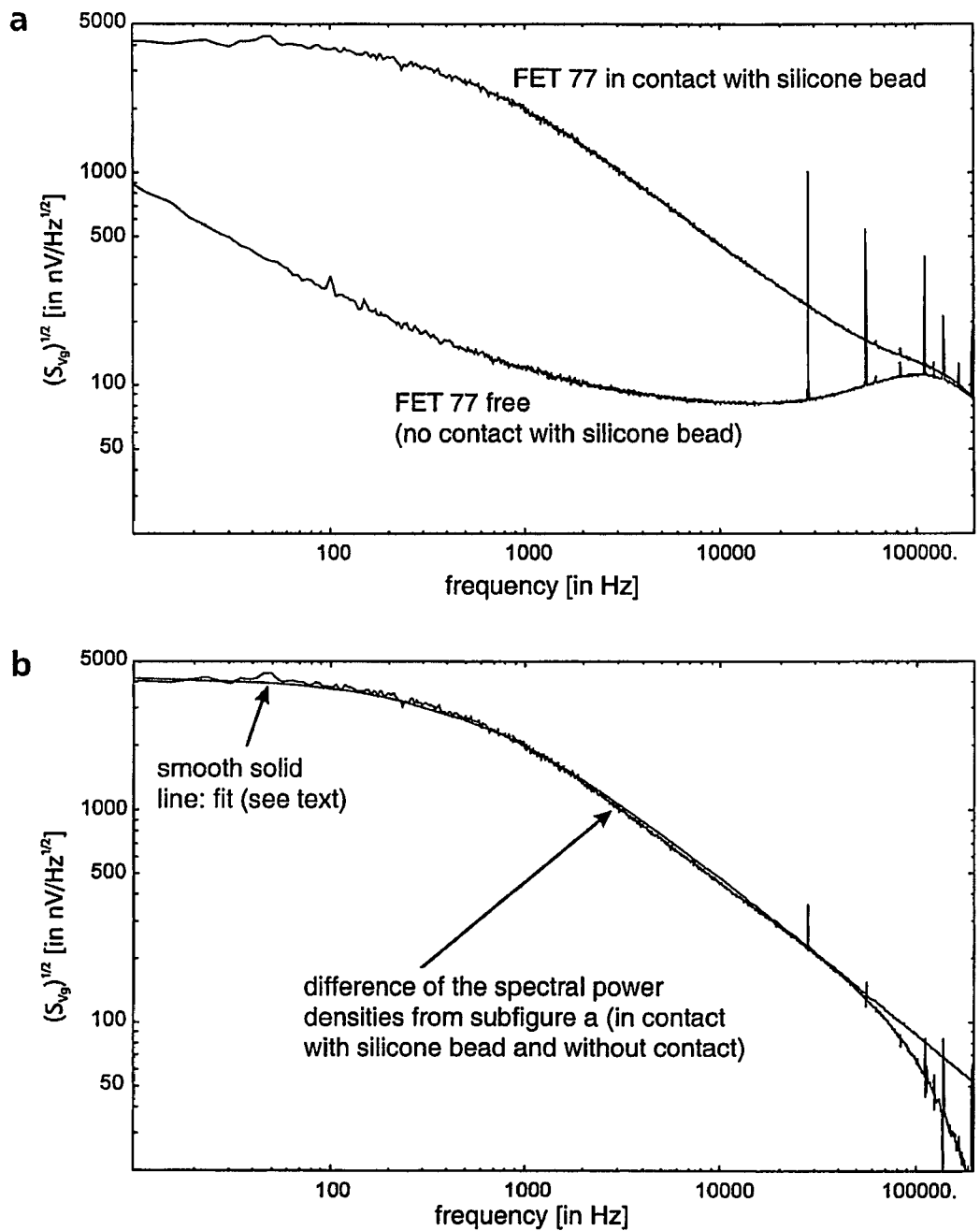

FIG. 8: (a) spectral power densities of the gate voltage of FET 77 with and without contact with a silicone bead. (b) The difference between the power densities of (a). This corresponds to the noise which is caused by the sealing impedance. The solid line is a fitted function (see Example 1). Following the convention, the square roots of the spectral power densities are plotted in (a) and (b).

Figure 9:
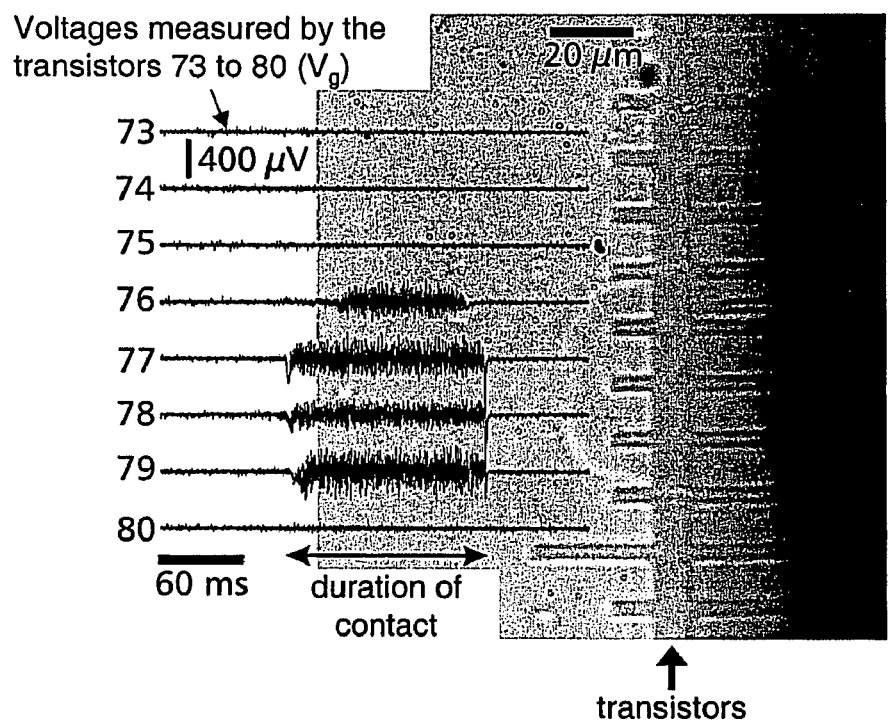

FIG. 9: the contact is produced only briefly, and is then disconnected again. The frequency range of the illustrated transistor signals is 400 to 10 000 Hz.

Figure 10:
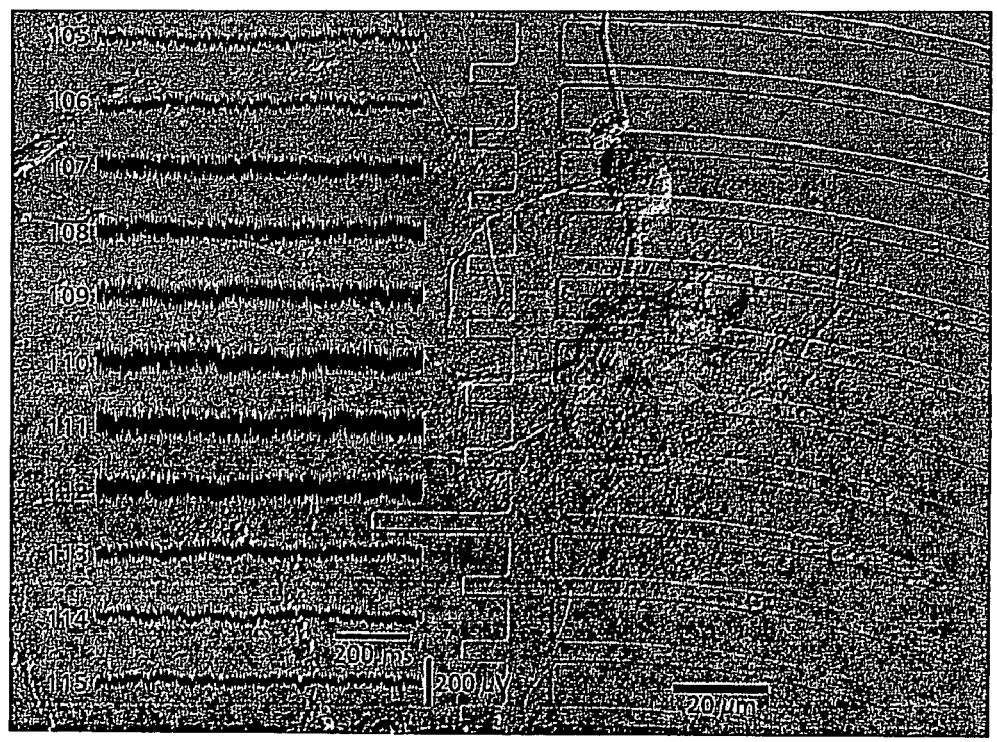

FIG. 10: shows an adhered cell on a silicon chip with field-effect transistors, to the left alongside this the gate-related voltage signals of the individual transistors. The noise is greatly increased in the area of the adhered cell.

Figure 11:
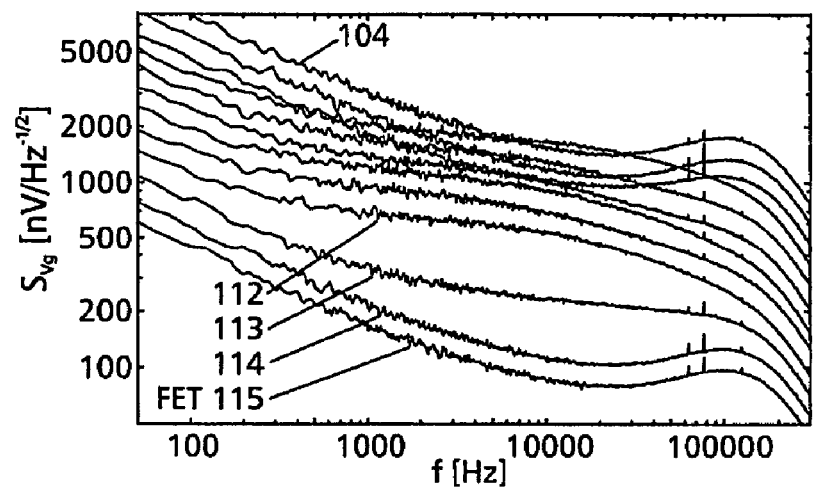

FIG. 11: shows the spectral power densities of the gate-related voltage noise of the transistors 104 to 115. In order to make the illustration clearer, the power densities are each offset by a factor of 1.3, and the scale relates to the lowermost curve. Both in the low-frequency range (below about 300 Hz) and in the high-frequency range (above about 30 000 Hz), the power density is dominated by the transistor noise, and is the same for all the transistors. The additional noise caused by adhesion is evident in the region from about 300 to about 30 000 Hz.

Figure 12:
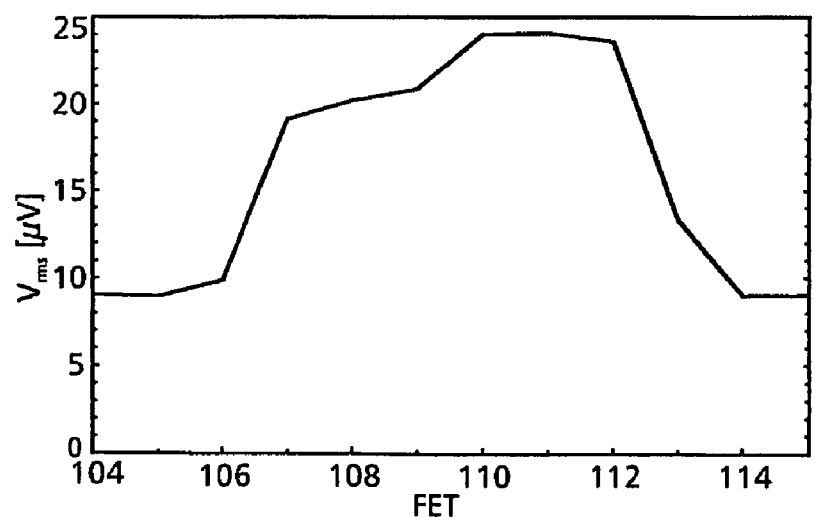

FIG. 12: by way of example, a characteristic variable $V_{rms}$ can be defined as the square root of the integral of the spectral power density from about 2 to about 10 kHz in order to characterize the impedance of the sealing. This characteristic variable correlates very well with the coverage by the adhered cell. The profile of the sealing is obtained directly, from a graphical plot.

EXAMPLE 1

Silicone Bead Pressed onto a Surface

Silicon chips with field-effect transistors were used, in which case both the voltage-sensitive gate areas and the rest of the chip were covered by silicon dioxide with the thickness of 10 nm. The transistors used had an approximately square gate area of about 6 μm×7 μm.

The drain current of the transistors was converted to a voltage by means of a current/voltage converter, comprising an OPA627 operational amplifier and a 100 kOhm feedback resistance, was amplified by a factor of 1000, was digitalized using a measurement card, and was recorded by a PC. In order to record the voltage signals as shown in FIGS. 7, 9 and 10, the signal was filtered by means of a 10 kHz low-pass filter, and was recorded at 30 kSample/s. The full amplifier bandwidth was used for the spectral power densities in FIGS. 8 and 11, effectively corresponding to a low-pass filter of 100 kHz, and with a digitization rate of 1 MSample/s.

The case of an insulating object which is brought actively into contact with a transistor array, is considered. FIG. 2 shows the schematic construction. The object insulated the gap at the top, so that the sealing impedance was formed from the conductivity of the gap, the capacitance of the substrate and the leakage conductance—which was thus present—of the substrate.

An experiment demonstrates this constellation. An approximately spherical bead of silicone with a diameter of about 600 μm was used as the insulating object, was supported at the tip of a canular and was moved by means of a finely controllable micromanipulator over a silicon chip with two linear arrays composed of field-effect transistors (FIG. 6). Normal electrophysiological solution with a conductivity of 15 mS/cm was used as the electrolyte.

The silicone bead was slowly lowered onto the transistor surface, until contact was made. Since the silicone bead was transparent, the Newton interference rings created by the contact could be seen using a microscope (detailed view in FIG. 6).

Greatly increased noise was evident on those transistors which were in contact with the silicone bead and were sealed by it (FIG. 7). The spectral power density provided more detailed information. For this purpose, the spectral power densities of the noise from the FET 77 were recorded when in contact and when not in contact (that is to say with the silicone bead removed again) (FIG. 8a). The difference between these power densities was formed for analysis (FIG. 8b), because this difference corresponds precisely to the noise from the sealing impedance. This is constant at low frequencies and falls at $f^{3/2}$ above a cut-off frequency. This is the profile which can be predicted from a continuous description of the noise in the gap. The solid line in FIG. 8b is a fit in the form $$S_{fit}(f) = 4k_B T \cdot R \frac{1}{1 + (f/f_0)^{3/2}} \tag{XI}$$

with the fitted values $$R=1.1 G\Omega, f_0=580 \text{ Hz} \tag{XII}.$$

The formation of the contact could be followed in real time. For this purpose, the silicone bead was brought briefly into contact with the transistor array, and was then removed again. FIG. 9 shows how the noise rose sharply and then also fell again within a few milliseconds. The propagation of the contact area over time can also be seen: FETs 77 and 78 made contact first of all, closely followed by FET 79 and, with a considerable delay, FET 76. This is also to be expected since the silicone bead which was lowered from above first of all touched the surface only with its "tip" and was then pressed flat as it was brought closer, thus enlarging the contact area and making contact with the adjacent transistors.

EXAMPLE 2

Cell on a Transistor Array

The sealing can be caused by a cell which has adhered to the substrate or the electrode. FIG. 3 shows this situation schematically. The cell membrane has a high impedance, so that the sealing impedance is governed primarily by the conductivity of the electrolyte and the width of the gap between the cell membrane and the substrate surface. The upper face of the lower cell membrane is at the rest potential of the cell interior, which is adjusted by the cell. The cell interior is once again in contact with the surrounding electrolyte via the upper membrane and its leakage conductance and capacitive susceptance.

The test construction used in this example corresponded to the test construction in Example 1.

FIG. 10 shows a cell from the hippocampus of a rat after being cultured for 16 days. The cell adheres to the substrate (the chip). The transistors which were covered by the cell exhibited increased noise. The spectral power densities in FIG. 11 show that the additional noise caused by the sealing by the cell can best be detected in the range between 300 and 30 000 Hz. In order to somewhat simplify the interpretation of the power densities, a frequency range [$f_1$, $f_2$] can be selected, with the noise contained in this range being converted to an effective characteristic variable $V_{rms}$ whose dimension is volts:

$$V_{rms} := \sqrt{\int_{f_1}^{f_2} S_v(f) df} . \tag{VIII}$$

This is illustrated in FIG. 12 for the spectral power densities from FIG. 11 in the frequency range from 2 to 10 kHz. This results in a sealing profile.

This example shows how the method according to the invention and an apparatus according to the invention can advantageously be used with electrode arrays with high spatial resolution.

EXAMPLE 3

Dense Cell Array Composed of Epithelium Cells

Epithelia play a highly important role in all relatively highly developed living beings: they ensure the separation of areas internal to the body and external to the body, and control the transport of substances (water, ions, proteins etc.) into and out of the body. Epithelia are generally single layers of specialized cells which combine to form a continuous (confluent) layer and form specialized contacts, the so-called "tight junctions", between the individual cells. These contacts are distinguished in that the membranes of the adjacent cells are very close, and thus form a barrier between the space above and underneath the cells.

FIG. 4 shows the construction schematically. The impedance which is caused by the tight junctions contributes considerably to the sealing impedance. In the case of a healthy and stable cell layer, it can be assumed that the adhesion to the substrate remains relatively constant, so that variations in the sealing impedance can be mainly associated with the tight junctions. The regulation of the tight junctions can thus be observed in real time.

The epithelium cells can form a concentration gradient between the upper face and lower face, that is to say enrichment or depletion of specific substances takes place in the gap between the cell layer and the substrate, in particular of ions, thus influencing the gap $r_s$ and hence the sealing impedance. Because of the high time resolution of the method, it could also be possible to observe a build-up of a concentration gradient caused by the cells.

EXAMPLE 4

Lipid Membrane with Incorporated Trans-Membrane Proteins

In the case of a lipid double membrane, also referred to as a "supported lipid bilayer", the adhesion impedance is formed from the gap $r_s$ and from the capacitance $c_m$ and the leakage conductance $g_l$ of the lipid membrane (FIG. 5). A lipid membrane represents a simple model system for the membranes of biological cells. In particular, membrane proteins and ion channels can be incorporated and their reaction to messenger substances can be investigated, if the leakage conductance of the membrane is influenced in this process.

Biosensors can thus be formed specifically with ion channels: as a result of the use of ligand-controlled ion channels, the ligand would influence the opening probability of the channels, and hence the sealing impedance. Since a large number of ligand-controlled ion channels exist and further types can be produced by genetic methods, this allows a large number of specific biosensors to be realized.

The invention claimed is:

1. A method for determining the sealing of a substance on a support, comprising
   (a) providing a substance on a support comprising at least one first electrode in contact with an electrically conductive liquid, wherein the substance entirely or partially covers the at least one first electrode,
   (b) determining the electrical noise of the sealing impedance between the at least one first electrode and a second electrode independently from external voltage, wherein essentially no current flows via the boundary surface of the at least one first electrode and the second electrode to the electrically conductive liquid, and
   (c) determining the sealing of the substance on the support from the electrical noise.

2. The method as claimed in claim 1, further comprising
   (d) determining the adhesion of the substance on the support from the sealing of the substance on the support.

3. The method as claimed in claim 1, wherein the support comprises a plurality of first electrodes.

4. The method as claimed in claim 1, wherein determination of the noise in (b) is carried out essentially without applying any voltage and any current between the at least one first and the second electrode.

5. The method as claimed in claim 1, wherein the sealing of the substance on the support is determined in (c) from the intensity of the noise.

6. The method as claimed claim 1, wherein the electrical noise of the impedance is determined in (b) as a noise voltage.

7. The method as claimed in claim 6, wherein the sealing of the substance on the support is determined in (c) from the peak-to-peak amplitude of the noise voltage in a predetermined frequency range $f_1$ to $f_2$.

8. An apparatus for carrying out the method as claimed in claim 1, comprising
   (i) a support for holding a substance, comprising at least one first electrode in contact with an electrically conductive liquid,
   (ii) mechanism suitable for measuring the electrical noise of the impedance between the at least one first electrode and the second electrode independently from external voltage and wherein essentially no current flows via the boundary surface of the at least one first electrode and the second electrode to the electrically conductive liquid, and
   (iii) mechanism suitable for determining the sealing of the substance on the support from the electrical noise.

9. The apparatus as claimed in claim 8, further comprising:
   (iv) mechanism suitable for determining the adhesion of the substance on the support from the sealing of the substance on the support.

10. The method as claimed in claim 6, wherein (c) comprises:
    (c1) determining the impedance from the noise voltage, and
    (c2) determining the sealing of the substance on the support from the impedance.

11. The method as claimed in claim 10, wherein the impedance is determined in (c1) from the time-dependent noise voltage.

12. The method as claimed in claim 6, wherein (c) comprises:
    (c1) determining the spectral power density from the noise voltage, and
    (c2) determining the sealing of the substance on the support from the spectral power density.

13. The method as claimed in claim 12, wherein the spectral power density is determined in (c1) from the time-dependent noise voltage.

14. The method as claimed in claim 12, wherein the sealing is determined in (c2) from the integral of the spectral power density over a predetermined frequency range $f_1$ to $f_2$ and/or from the square root of the integral of the spectral power density over a predetermined frequency range $f_1$ to $f_2$.

15. The method as claimed in claim 1, wherein the noise is determined in a frequency range from about 100 Hz to about 100 kHz, or in a subregion thereof.

16. The method as claimed in claim 1, wherein (b) and (c) are carried out with a time interval between them.

17. The method as claimed in claim 1, wherein the substance is a biological cell, a biological cell group, a biological cell culture or a lipid membrane.

18. The method as claimed in claim 17, wherein the biological cell group or the biological cell culture forms a single-cell layer, a confluent single-cell layer, or a multiple-cell layer.

19. The method as claimed in claim 1, wherein the substance is a lipid layer, which may contain proteins.

20. The method as claimed in claim 1, wherein the at least one first electrode is a transistor, a field-effect transistor, or a metal electrode.

21. The method as claimed in claim 20, wherein the at least one first electrode covers a support area of at most 10 000 µm².

22. The method as claimed in claim 1, wherein the second electrode is an Ag/AgCl electrode, or is a transistor, a field-effect transistor, or a metal electrode.

23. The method as claimed in claim 1, wherein the electrically conductive liquid is a saline solution or a cell culture medium.

24. The method as claimed in claim 1, wherein the support is formed from silicon, glass, a polymer, GaAs and GaN, sapphire and/or composite materials formed from these materials.

25. The method as claimed in claim 17, wherein the biological cell, the biological cell culture or the biological cell group is cultivated on the support.

26. An apparatus for carrying out the method as claimed in claim 1, comprising
 (i) a support for holding a substance, comprising at least one first electrode in contact with an electrically conductive liquid,
 (ii) means for measuring the electrical noise of the impedance between the at least one first electrode and the second electrode independently from external voltage and wherein essentially no current flows via the boundary surface of the at least one first electrode and the second electrode to the electrically conductive liquid, and
 (iii) means for determining the sealing of the substance on the support from the electrical noise.

27. The apparatus as claimed in claim 26, further comprising:
 (iv) means for determining the adhesion of the substance on the support from the sealing of the substance on the support.

28. The apparatus as claimed in claim 26, wherein the support comprises a plurality of first electrodes.

29. The apparatus as claimed in claim 26, wherein the means (ii) and (iii) are designed such that they can be used with a time interval between them.

30. A method for identifying a compound which modulates the sealing of a substance on a support, comprising:
 (A)
 (I)
 determining the sealing of the substance on a support by a method (X) which comprises
  (a) providing a substance on a support comprising at least one first electrode in contact with an electrically conductive liquid, wherein the substance entirely or partially covers the at least one first electrode,
  (b) determining the electrical noise of the impedance between the at least one first electrode and a second electrode, wherein essentially no current flows via the boundary surface of the at least one first electrode and the second electrode to the electrically conductive liquid, and
  (c) determining the sealing of the substance on the support from the electrical noise,
 and/or
 using an apparatus (XX) comprising
  (i) a support for holding a substance, comprising at least one first electrode in contact with an electrically conductive liquid,
  (ii) means for measuring the electrical noise of the impedance between the at least one first electrode and a second electrode independently from external voltage and wherein essentially no current flows via the boundary surface of the at least one first electrode and the second electrode to the electrically conductive liquid, and
  (iii) means for determining the sealing of the substance on the support from the electrical noise, in the absence of the compound to be investigated,
 (II)
 determining the sealing of the substance on a support using the method (X) and/or using said apparatus (XX) in the presence of the compound to be investigated, and
 (III)
 selecting a compound which modulates the sealing of the substance on the support in a predetermined manner;
 or
 (B)
 (1)
 determining the adhesion of the substance on a support by a method (Y) which comprises
  (a) providing a substance on a support comprising at least one first electrode in contact with an electrically conductive liquid, wherein the substance entirely or partially covers the at least one first electrode,
  (b) determining the electrical noise of the impedance between the at least one first electrode and a second electrode, wherein essentially no current flows via the boundary surface of the at least one first electrode and the second electrode to the electrically conductive liquid,
  (c) determining the sealing of the substance on the support from the electrical noise, and
  (d) determining the adhesion of the substance on the support from the sealing of the substance on the support,
 and/or
 using an apparatus (YY) comprising
  (i) a support for holding a substance, comprising at least one first electrode in contact with an electrically conductive liquid,
  (ii) means for measuring the electrical noise of the impedance between the at least one first electrode and a second electrode independently from external voltage and wherein essentially no current flows via the boundary surface of the at least one first electrode and the second electrode to the electrically conductive liquid, and
  (iii) means for determining the sealing of the substance on the support from the electrical noise, and (iv) means for determining the adhesion of the substance on the support from the sealing of the substance on the support, in the absence of the compound to be investigated, (2) determining the adhesion of the substance on a support using the method (Y) and/or using said apparatus (YY) in the presence of the compound to be investigated, and (3) selecting a compound which modulates the adhesion of the substance on the support in a predetermined manner.

31. A method according to claim 30, wherein in method (X) or (Y), (b) comprises determining the electrical noise of the sealing impedance between the at least one first electrode and the second electrode independently from external voltage.

32. A method for identifying a compound which modulates the adhesion of a substance on a support according to claim 30, comprising:

(B)

(1) determining the adhesion of the substance on a support by a method (Y) which comprises (a) providing a substance on a support comprising at least one first electrode in contact with an electrically conductive liquid, wherein the substance entirely or partially covers the at least one first electrode, (b) determining the electrical noise of the impedance between the at least one first electrode and the second electrode, wherein essentially no current flows via the boundary surface of the at least one first electrode and the second electrode to the electrically conductive liquid, (c) determining the sealing of the substance on the support from the electrical noise, and (d) determining the adhesion of the substance on the support from the sealing of the substance on the support, and/or using an apparatus (YY) comprising (i) a support for holding a substance, comprising at least one first electrode in contact with an electrically conductive liquid, (ii) means for measuring the electrical noise of the impedance between the at least one first electrode and a second electrode independently from external voltage and wherein essentially no current flows via the boundary surface of the at least one first electrode and the second electrode to the electrically conductive liquid, and (iii) means for determining the sealing of the substance on the support from the electrical noise, and (iv) means for determining the adhesion of the substance on the support from the sealing of the substance on the support, in the absence of the compound to be investigated, (2) determining the adhesion of the substance on a support using the method (Y) and/or using said apparatus (YY) in the presence of the compound to be investigated, and (3) selecting a compound which modulates the adhesion of the substance on the support in a predetermined manner.

33. A method for identifying a compound which modulates the sealing of a substance on a support according to claim 30, comprising:

(A)

(I) determining the sealing of the substance on a support by a method (X) which comprises (a) providing a substance on a support comprising at least one first electrode in contact with an electrically conductive liquid, wherein the substance entirely or partially covers the at least one first electrode, (b) determining the electrical noise of the impedance between the at least one first electrode and the second electrode, wherein essentially no current flows via the boundary surface of the at least one first electrode and the second electrode to the electrically conductive liquid, and (c) determining the sealing of the substance on the support from the electrical noise, and/or using an apparatus (XX) comprising (i) a support for holding a substance, comprising at least one first electrode in contact with an electrically conductive liquid, (ii) means for measuring the electrical noise of the impedance between the at least one first electrode and a second electrode independently from external voltage and wherein essentially no current flows via the boundary surface of the at least one first electrode and the second electrode to the electrically conductive liquid, and (iii) means for determining the sealing of the substance on the support from the electrical noise, in the absence of the compound to be investigated, (II) determining the sealing of the substance on a support using the method (X) and/or using said apparatus (XX) in the presence of the compound to be investigated, and (III) selecting a compound which modulates the sealing of the substance on the support in a predetermined manner.

34. In a method for diagnosis of a malignant tumor, wherein the improvement comprises determining the sealing of a malignant tumor cell on a support, which determination comprises (a) providing a malignant tumor cell on a support comprising at least one first electrode in contact with an electrically conductive liquid, wherein the malignant tumor cell entirely or partially covers the at least one first electrode, (b) determining the electrical noise of the sealing impedance between the at least one first electrode and a second electrode independently from external voltage, wherein essentially no current flows via the boundary surface of the at least one first electrode and the second electrode to the electrically conductive liquid, and (c) determining the sealing of the malignant tumor cell on the support from the electrical noise.

35. A method for determining the sealing of a substance on a support, comprising (a) providing a substance on a support comprising at least one first electrode in contact with an electrically conductive liquid, wherein the substance entirely or partially covers the at least one first electrode, (b) determining the electrical noise of the impedance as a noise voltage between the at least one first electrode and a second electrode, and (c) determining the sealing of the substance on the support from the electrical noise (a) from the amplitude of the noise voltage in a predetermined frequency range $f_1$ to $f_2$, and wherein the amplitude is characterized by the voltage range in which the electrical noise voltage moves for up to 95% of a predetermined time period, or (b) from the amplitude of the noise voltage in a predetermined frequency range $f_1$ to $f_2$, and wherein the amplitude of the noise voltage is characterized by ±3.2 σ.

36. The method as claimed in claim 35, wherein the sealing of the substance on the support is determined in (c) from the amplitude of the noise voltage in a predetermined frequency range $f_1$ to $f_2$, and wherein the amplitude is characterized by the voltage range in which the electrical noise voltage moves for up to 95% of a predetermined time period.

37. The method as claimed in claim 35, wherein the sealing of the substance on the support is determined in (c) from the amplitude of the noise voltage in a predetermined frequency range $f_1$ to $f_2$, and wherein the amplitude of the noise voltage is characterized by ±3.2 σ.

38. A method according to claim 35, wherein (b) comprises determining the electrical noise of the sealing impedance as a noise voltage between the at least one first electrode and the second electrode independently from external voltage.

* * * * *